United States Patent
Fisher et al.

(10) Patent No.: US 6,622,725 B1
(45) Date of Patent: Sep. 23, 2003

(54) REBREATHING CIRCUIT TO SET AND STABILIZE END TIDAL AND ARTERIAL $PCO_2$ DESPITE VARYING LEVELS OF MINUTE VENTILATION

(76) Inventors: Joseph A. Fisher, 113 Franmore Circle, Thornhill, Ontario (CA), L4J 3B9; Alex Vesely, P.O. Box 622, Station Q, Toronto, Ontario (CA), M4T 2N4; Hiroshi Sasano, 5875 Yonge Street, Suite 505, Toronto, Ontario (CA), M2M 4J2; George Volgyesi, 36 Gatehead Road, Toronto, Ontar (CA), M2J 2P5; Janet Tesler, 118 Old Surrey Lane., Richmond Hill, Ontario (CA), L4C 8S6

( * ) Notice: Subject to any disclaimer, the term of this patent is extended or adjusted under 35 U.S.C. 154(b) by 271 days.

(21) Appl. No.: 09/676,899

(22) Filed: Oct. 2, 2000

(30) Foreign Application Priority Data

Mar. 31, 2000 (CA) .............................................. 2304292

(51) Int. Cl.[7] .............................................. A61M 15/08
(52) U.S. Cl. ............................ 128/204.21; 128/203.12
(58) Field of Search ...................... 128/204.18, 204.21, 128/204.22, 204.23, 204.26, 204.28, 204.29, 205.13–205.17, 205.24, 205.11, 200.22, 200.24, 203.12, 203.13, 203.28, 205.18, 910, 911

(56) References Cited

U.S. PATENT DOCUMENTS

| | | | | |
|---|---|---|---|---|
| 3,901,230 A | * | 8/1975 | Henkin ................... | 128/205.17 |
| 4,051,847 A | * | 10/1977 | Henkin ................... | 128/202.22 |
| 4,112,938 A | * | 9/1978 | Jeretin .................... | 128/204.23 |
| 4,188,946 A | * | 2/1980 | Watson et al. .......... | 128/204.22 |
| 4,543,951 A | * | 10/1985 | Phuc ..................... | 128/204.25 |
| 4,596,246 A | * | 6/1986 | Lyall ..................... | 128/202.27 |
| 4,617,924 A | * | 10/1986 | Heim et al. ............ | 128/204.23 |
| 4,676,239 A | * | 6/1987 | Humphrey ............. | 128/203.28 |
| 4,991,576 A | * | 2/1991 | Henkin et al. ......... | 128/202.27 |
| 5,245,996 A | * | 9/1993 | Manicom ............... | 128/205.24 |
| 5,320,093 A | | 6/1994 | Raemer | |
| 5,400,778 A | * | 3/1995 | Jonson et al. .......... | 128/204.23 |
| 5,647,345 A | * | 7/1997 | Saul ...................... | 128/201.23 |
| 5,664,562 A | * | 9/1997 | Bourdon ................ | 128/204.18 |
| 5,673,688 A | * | 10/1997 | Tham et al. ........... | 128/204.22 |
| 5,694,924 A | * | 12/1997 | Cewers .................. | 128/204.21 |
| 5,740,796 A | * | 4/1998 | Skog .................... | 128/204.23 |
| 5,752,506 A | * | 5/1998 | Richardson ............ | 128/204.18 |
| 5,797,393 A | * | 8/1998 | Kohl ..................... | 128/204.23 |
| 5,803,064 A | * | 9/1998 | Phelps et al. .......... | 128/203.12 |
| 5,875,783 A | * | 3/1999 | Kullik ................... | 128/204.18 |
| 5,957,129 A | * | 9/1999 | Tham et al. ........... | 128/204.22 |
| 6,003,511 A | * | 12/1999 | Fukunaga et al. ..... | 128/202.27 |
| 6,009,871 A | * | 1/2000 | Kiske et al. ........... | 128/203.12 |
| 6,119,686 A | * | 9/2000 | Somerson et al. ..... | 128/202.22 |
| 6,125,848 A | * | 10/2000 | Hendrickson et al. . | 128/204.22 |
| 6,210,342 B1 | * | 4/2001 | Kuck et al. ............ | 128/204.23 |
| 6,227,196 B1 | * | 5/2001 | Jaffe et al. ............. | 128/200.26 |
| 6,298,848 B1 | * | 10/2001 | Skog ..................... | 128/204.18 |
| 6,306,098 B1 | * | 10/2001 | Orr et al. ............... | 128/200.26 |
| 6,354,292 B1 | * | 3/2002 | Fisher ................... | 128/203.12 |
| 6,408,847 B1 | * | 6/2002 | Nuckols et al. ........ | 128/204.18 |
| 6,422,237 B1 | * | 7/2002 | Engel et al. ........... | 128/204.18 |
| 6,439,231 B1 | * | 8/2002 | Fukunaga et al. ..... | 128/202.27 |

FOREIGN PATENT DOCUMENTS

| | | | |
|---|---|---|---|
| WO | WO 92/05826 | * | 4/1992 |
| WO | PCT/SE96/00644 | | 11/1996 |
| WO | WO 96/36385 | * | 11/1996 |
| WO | PCT/CA97/00186 | | 9/1998 |

* cited by examiner

Primary Examiner—Weilun Lo
Assistant Examiner—Teena Mitchell
(74) Attorney, Agent, or Firm—Stetina Brunda Garred & Brucker

(57) ABSTRACT

A method of controlling $PCO_2$ in a patient at a predetermined desired level(s) comprising a breathing circuit which is capable of organizing exhaled gas so as to be preferentially inhaled during re-breathing when necessary by providing alveolar gas for re-breathing in preference to dead space gas.

20 Claims, 1 Drawing Sheet

REBREATHING CIRCUIT TO SET AND STABILIZE END TIDAL AND ARTERIAL PCO$_2$ DESPITE VARYING LEVELS OF MINUTE VENTILATION

CROSS-REFERENCE TO RELATED APPLICATIONS

This Application claims priority to Canadian Application Serial No. 2304292 filed Mar. 31, 2000.

STATEMENT RE FEDERALLY SPONSORED RESEARCH/DEVELOPMENT

[Not Applicable]

BACKGROUND OF INVENTION

Physiology

Venous blood returns to the heart from the muscles and organs depleted of oxygen (O$_2$) and full of carbon dioxide (CO$_2$). Blood from various parts of the body is mixed in the heart (mixed venous blood) and pumped to the lungs. In the lungs the blood vessels break up into a net of small vessels surrounding tiny lung sacs (alveoli). The net sum of vessels surrounding the alveoli provides a large surface area for the exchange of gases by diffusion along their concentration gradients. A concentration gradient exists between the partial pressure of CO$_2$ (PCO$_2$) in the mixed venous blood (PvCO$_2$) and the alveolar PCO$_2$. The CO$_2$ diffuses into the alveoli from the mixed venous blood from the beginning of inspiration until an equilibrium is reached between the PvCO$_2$ and the alveolar PCO$_2$ at some time during the breath. When the subject exhales, the first gas that is exhaled comes from the trachea and major bronchi which do not allow gas exchange and therefore will have a gas composition similar to the inhaled gas. The gas at the end of this exhalation is considered to have come from the alveoli and reflects the equilibrium CO$_2$ concentration between the capillaries and the alveoli; the PCO$_2$ in this gas is called end-tidal PCO$_2$ (PetCO$_2$).

When the blood passes the alveoli and is pumped by the heart to the arteries it is known as the arterial PCO$_2$ (PaCO$_2$). The arterial blood has a PCO$_2$ equal to the PCO$_2$ at equilibrium between the capillaries and the alveoli. With each breath some CO$_2$ is eliminated from the lung and fresh air containing little or no CO$_2$ (CO$_2$ concentration is assumed to be 0) is inhaled and dilutes the residual alveolar PCO$_2$, establishing a new gradient for CO$_2$ to diffuse out of the mixed venous blood into the alveoli. The rate of breathing, or ventilation (V), usually expressed in L/min, is exactly that required to eliminate the CO$_2$ brought to the lungs and maintain an equilibrium PCO$_2$ (and PaCO$_2$) of approximately 40 mmHg (in normal humans). When one produces more CO$_2$ (e.g., as a result of fever or exercise), more CO$_2$ is produced and carried to the lungs. One then has to breathe harder (hyperventilate) to wash out the extra CO$_2$ from the alveoli, and thus maintain the same equilibrium PaCO$_2$. But if the CO$_2$ production stays normal, and one hyperventilates, then the PaCO$_2$ falls. Conversely, if CO$_2$ production stays constant and ventilation falls, arterial PCO$_2$ rises.

It is important to note that not all V contributes to blowing off CO$_2$. Some V goes to the air passages (trachea and major bronchi) and alveoli with little blood perfusing them, and thus doesn't contribute to blowing off CO$_2$. This V is termed "dead space" ventilation and gas in the lung that has not participated in gas exchange with the blood is called "dead space" gas. That portion of V that goes to well perfused alveoli and participates in gas exchange is called the alveolar ventilation (VA) and exhaled gas that had participated in gas exchange in the alveoli is termed "alveolar gas".

Referring to the PCT Application No. WO98/41266 filed by Joe Fisher (WO98/41266), there is taught a method of accelerating the resuscitation of a patient having been anaesthetized by providing the patient with a source of fresh gas and a source of reserve gas. When the patient breathes at a rate less than or equal to the fresh gas flowing into the circuit, all of the inhaled gas is made up of fresh gas. When the patient's minute ventilation exceeds the fresh gas flow, the inhaled gas is made up of all of the fresh gas and the additional gas is provided by "reserve gas" consisting of a composition similar to the fresh gas plus CO$_2$ such that the concentration of CO$_2$ in the reserve gas of about 6% is such that its partial pressure is equal to the partial pressure of CO$_2$ in the mixed venous blood. At no time while using this method will the patient rebreathe gas containing anaesthetic. In order to accelerate the resuscitation of the patient, a source of fresh gas is provided for normal levels of minute ventilation, typically 5 L per minute and a supply of reserve gas is provided for levels of ventilation above 5 L per minute wherein the source of reserve gas includes approximately 6% carbon dioxide having a PCO$_2$ level substantially equal to that of mixed venous blood. It has been found that this method and various circuits and processes for implementing the method are advantageous not only for resuscitating individuals from surgery, but also to deal with carbon monoxide poisoning or the like as taught in the application. By allowing increased ventilation yet maintaining the PCO$_2$ level substantially equal to that prior to the increased ventilation, it has been found that in utilizing the method, maximum benefits of gas elimination are achieved without changing the CO$_2$ levels in the patient. However, one limitation is that a source of reserve gas and its delivery apparatus must be supplied to pursue the method and that the reserve gas must be at about 6% CO$_2$ concentration substantially having a PCO$_2$ equal to that of mixed venous blood or about 46 mmHg.

To simplify the circuit taught by Fisher (WO98/41266), the reserve gas can be replaced by previously exhaled gas. The gas at the end of exhalation has substantially equilibrated with mixed venous gas and thus has a PCO$_2$ substantially equal to it. However, if rebreathed gas is used instead of separately constituted reserve gas to prevent the decrease in PCO$_2$ with increased ventilation, the anesthetic and CO will also be rebreathed and their elimination will not be enhanced. There are other applications for a circuit that maintains PCO$_2$ constant with increased ventilation which are not invalidated by using exhaled gas as the reserved gas which are listed hereinafter.

Discussion of Prior Art Circuits Used for Rebreathing

Prior art circuits used to prevent decreased in PCO$_2$ resulting from increased ventilation, by means of rebreathing of previously exhaled gas are described according to the location of the fresh gas inlet, reservoir and pressure relief valve with respect to the patient. They have been classified by Mapleson and are described in Dorsch and Dorsch pg 168.

1. Maintenance of constant CO$_2$ with increased minute ventilation.

Mapleson A

The circuit comprises a pressure relief valve nearest the patient, a tubular reservoir and fresh gas inlet distal to the patient. In this circuit, on expiration, dead space gas is retained in the circuit, and after the reservoir becomes full, alveolar gas is lost through the relief valve. Dead space gas is therefore preferentially rebreathed. Dead space gas has a $PCO_2$ much less than mixed venous $PCO_2$. This is less effective in maintaining $PCO_2$ than rebreathing alveolar gas, as occurs with the circuit of the present invention.

Mapleson B, C

The circuit includes a relief valve nearest the patient, and a reservoir with a fresh gas inlet at the near patient port. As with Mapleson A, dead space gas is preferentially rebreathed when minute ventilation exceeds fresh gas flow. In addition, if minute ventilation is temporarily less than fresh gas flow, fresh gas is lost from the circuit due to the proximity of the fresh gas inlet to the relief valve. Under these conditions, when ventilation once again increases there is no compensation for transient decrease in ventilation as the loss of fresh gas will prevent a compensatory decrease in $PCO_2$.

With the present invention circuit, when minute ventilation temporarily is less than fresh gas flow, no fresh gas is lost from the circuit. Instead, the reservoir acts as a buffer, storing the extra fresh gas, and when ventilation increases once more, breathing the accumulated fresh gas allows $PCO_2$ to return to the previous level.

Mapleson D and E

Mapleson D consists of a circuit where fresh gas flow enters near the patient port, and gas exits from a pressure relief valve separated from the patient port by a length of reservoir tubing. Mapleson E is similar except it has no pressure relief valve allowing the gas to simply exit from an opening in the reservoir tubing. In both circuits, fresh gas is lost without being first breathed. The volume of gas lost without being breathed at a given fresh gas flow is dependent on the minute ventilation such that only at infinite ventilation is all the fresh gas used for alveolar ventilation. Thus the alveolar ventilation and the $PCO_2$ level are also dependent on the minute ventilation. Fresh gas is lost because during expiration, fresh gas mixes with expired gas and escapes with it from the exit port of the circuit. Furthermore, the amount of fresh gas lost is a function of expiratory time, and hence by changing the pattern of breathing, one can increase or decrease the proportion of fresh gas breathed. With our circuit, all of the fresh gas is breathed by the subject.

Circle anaesthetic circuit with $CO_2$ absorber removed.

There are many different possible configurations of fresh gas inlet, relief valve, reservoir bag and $CO_2$ absorber (see Dorsch and Dorsch, pg. 205–207). In all configurations, a mixture of expired gases enters the reservoir bag, and therefore rebreathed gas consists of combined dead space gas and alveolar gas. This is less efficient in maintaining $PCO_2$ constant than rebreathing alveolar gas preferentially as occurs with our circuit, especially at small increments of V above the fresh gas flow.

Circuit previously described by Fisher (WO98/41266)

Fisher (WO98/41266) has previously described a circuit that maintains $PCO_2$ independent of minute ventilation. Instead of making up the difference between fresh gas flow and minute ventilation with gas expired from a previous breath, Fisher (WO98/41266) requires an external source of $CO_2$. The circuit of the present invention exploits the same principle in maintaining $PCO_2$ constant, however it uses the patient's own previously expired $CO_2$ instead of externally provided $CO_2$. Thus the circuit is must less expensive to operate, more compact and portable and thus would be more practical for applications where the maintenance of $CO_2$ is desired but the elimination of other gases such as anesthetics and carbon monoxide is not required.

2. Changes in $CO_2$ or other gas

For other applications such as a) maintaining a constant $PCO_2$ or instituting two or more levels of arterial $PCO_2$ during nuclear magnetic resonance imaging, b) raising $PCO_2$ i) during pregnancy to improve placental blood flow, ii) to prevent shivering, iii) to increase tissue perfusion, and iv) protect tissues from oxidative damage, preventing rebreathing of exhaled gases is not necessary.

However, it would therefore be advantageous to reap the benefits of controlling the $PCO_2$ at a constant level and not having to incur the expense of supplying reserve gas. It has been determined that traumatized patients may be assisted in certain circumstances by maintaining the $PCO_2$ level substantially constant or increased. It has also been determined that various diagnostic procedures can be enhanced by pursuing the same. This heretofore was not contemplated in the prior art nor in the prior disclosure of Joseph Fisher (WO98/41266) discussed above.

It is therefore a primary objective of the present invention to provide a simplified method of controlling $PCO_2$ at a predetermined desired level. It is a further objective of the present invention to provide a simplified method of changing the $PCO_2$ of a patient by changing the fresh gas flow in the circuit.

It is a further objective of the present invention to provide a circuit to affect the method that prevents loss of fresh gas and that ensures that a patient breathing at a rate greater than the fresh gas flow receives all the fresh gas independent of the rate of pattern of breathing.

It is a further objective of the present invention to provide a breathing circuit that prevents rebreathing unless the minute ventilation exceeds the fresh gas flow.

It is yet a further objective of the present invention to provide a circuit where alveolar gas is rebreathed in preference to dead space gas.

It is a further objective of the present invention to provide an improved breathing circuit to be used to assist patients who have been traumatized or run the risk of being traumatized, or alternatively to enhance the results of diagnostic procedures, or the benefits of medical procedures.

It is a further object of the present invention to provide methods of treatment using the said circuit and the use of the said circuit to assist patients who have been traumatized or run the risk of being traumatized or alternatively to enhance the results of diagnostic procedures, or the benefits of medical procedures.

Further and other objectives of the present invention will become apparent to those skilled in the art when considering the following summary of the invention and the more detailed description of the preferred embodiments illustrated therein.

BRIEF SUMMARY OF INVENTION

According to a primary aspect of the invention there is provided a method of controlling $PCO_2$ in a patient at a predetermined desired level(s) comprising a breathing circuit which is capable of organizing exhaled gas so as to be preferentially inhaled during rebreathing when necessary by providing alveolar gas for rebreathing in preference to dead space gas. The preferred circuit in effecting the above-mentioned method includes a breathing port for inhaling and exhaling gas; a bifurcated conduit adjacent said port; preferably being substantially Y-shaped, and including a first and second conduit branch, with the first conduit branch including a fresh gas inlet, preferably oxygen, and a check valve disposed proximate the port. The check valve allows the passage of inhaled fresh gas to the port but closes during exhalation. The second conduit includes a check valve which allows passage of exhaled gas through the check valve but prevents flow back to the breathing port once the gas passes through the check valve. The first conduit branch has located proximate the terminus thereof, a fresh gas reservoir of predetermined size and preferably a flexible bag. The second conduit branch has located proximate the terminus thereof, an exhaled gas reservoir, preferably being a rigid tube having an open end and being preferably approximately 3 L in capacity. The terminus of said first and second conduit branches have extending there between an interconnecting conduit and has a check valve located therein. When minute ventilation for the patient is equal to the fresh gas flow, for example 5 liters/minute, fresh gas enters the breathing port from the first conduit branch at a predetermined rate and preferably 5 L per minute and is exhaled through the second conduit branch at a rate of preferably 5 L per minute; wherein the exhaled gas travels down the exhaled gas reservoir which preferentially provides that dead space gas be disposed nearest the open end of the reservoir and that alveolar gas would be located proximate the end of the reservoir nearest the terminus of the second conduit branch. When it is desirable for the minute ventilation to exceed the fresh gas flow, for example 5 L per minute, the patient will inhale expired gas retained in the expired gas reservoir which will pass through the check valve in the interconnecting conduit at a rate making up the shortfall in the fresh gas flow of, for example, 5 L per minute, wherein the shortfall differential is made up of rebreathed gas of which alveolar gas is preferentially rebreathed, thereby preventing a change in the $PCO_2$ level of alveolar gas despite the increased minute ventilation.

When setting the fresh gas flow to maintain a desired $PCO_2$ it is important that the fresh gas reservoir be allowed to first be depleted of gas until it just empties at the end of the inhalation cycle. In this way once it is desired to increase the minute ventilation, a slight negative pressure will exist in the interconnecting conduit during inhalation, opening its check valve and allowing further breathing gas beyond the normal level of ventilation to be supplied by previously exhaled gas.

There are many uses for this particular circuit which will be described hereinafter. There may be situations which exist when treating a patient wherein it is desirable to prevent hypocapnia in the patient. For example, in the case of a pregnant woman having great anxiety due to the pain during delivery, it is desirable not to have her hyperventilate so as to contract the blood vessels in the placenta causing potential insufficient blood flow to the baby. By using the above-mentioned circuit during labor, this can be avoided. It also may be advantageous to induce hypercapnea during diagnostic procedures to enhance the diagnostic procedure or alternatively when a patient undergoes treatment as in treatment with ionizing radiation, to increase the sensitivity of tissue to the treatment. This, for example, would occur during radiation treatment for cancerous cells.

According to yet another aspect of the invention, there is provided a method of enhancing the results of a diagnostic procedure or medical treatment comprising the steps of:

providing a circuit which is capable of organizing exhaled gas so as to provide to the patient preferential rebreathing of alveolar gas in preference to dead space gas (for example the circuit described above), when the patient is ventilating at a rate greater than the fresh gas flow, and when inducing hypercapnea is desired, by decreasing the fresh gas flow and passively providing a corresponding increase in rebreathed gas so as to prevent the $PCO_2$ level of arterial blood from dropping despite increases in minute ventilation;

continuing inducing hypercapnia until such time as the diagnostic or medical procedure is completed, wherein the results of said diagnostic or medical procedure are enhanced by carrying out the method in relation to the results of the procedure had the method not been carried out. Examples of such procedures would be MRI or radiation treatments or the like.

A method of treating or assisting a patient, preferably human, during a traumatic event characterized by hyperventilation comprising the steps of:

providing a circuit in which alveolar ventilation is equal to the fresh gas flow and increases in alveolar ventilation with increases in minute ventilation is prevented by a circuit (for example the preferred circuit described above) which is capable of organizing exhaled gas so as to provide to the patient preferential rebreathing alveolar gas in preference to dead space gas;

following ventilating the patient at a rate of normal minute ventilation, preferably approximately 5 L per minute, and when desired inducing hypercapnea so as to increase arterial $PCO_2$ and prevent the $PCO_2$ level of arterial blood from subsequently dropping below that achieved as a result of decreasing the fresh gas flow;

continuing maintaining normocapnia despite the ventilation at an increased rate until such time as the traumatic event and concomitant hyperventilation is completed, wherein the effects of hyperventilation experienced during the traumatic event are minimized, for example, the mother during labor becoming light headed or the baby during the delivery also being effected with the oxygen delivery to its brain being decreased as a result of contraction of the blood vessels in the placenta and fetal brain.

A list of circumstances in which the method enhancing the diagnostic procedure results or the experience of the traumatic event are listed below.

Applications of this method and circuit:

1. Maintenance of constant $PCO_2$ and inducing changes in $PCO_2$ during MRI;
2. Inducing and/or maintaining increased $PCO_2$
   a) to prevent or treat shivering and tremors during labor, post-anesthesia, hypothermia, and certain other pathological states;
   b) to treat fetal distress due to asphyxia;
   c) to induce cerebral vasodilatation, prevent cerebral vasospasm, and provide cerebral protection following subarachnoid hemorrhage, cerebral trauma and other pathological states;
   d) to increase tissue perfusion in tissues containing cancerous cells to increase their sensitivity to ionizing radiation and delivery of chemotherapeutic agents;
   e) to aid in radiodiagnostic procedures by providing contrast between tissues with normal and abnormal vascular response;
   f) protection of various organs such as the lung, kidney and brain during states of multi-organ failure.
3. Prevention of hypocapnia with $O_2$ therapy, especially in pregnant patients.
4. Other applications where $O_2$ therapy is desired and it is important to prevent the accompanying drop in $PCO_2$.

It has been found in carrying out the above-mentioned method and preferably with the preferred circuit described that by maintaining a constant $PCO_2$ level and inducing changes in $PCO_2$ during a diagnostic procedure such as an MRI, better quality pictures can be obtained. It is therefore provided, according to another aspect of the invention, that an improved method of creating MRI images is disclosed by following the above-mentioned method and particularly comprising the steps of maintaining a constant $PCO_2$ and inducing changes in that $PCO_2$ level during the MRI procedure in order to facilitate improvement in the quality of the pictures being taken. The method for inducing the changes in the $PCO_2$ include preferably using the above-mentioned circuit or any circuit known in the prior art and described in the background of the invention which might provide a substantial part or most of the benefits described herein. For example, the Mapleson D and E circuits predictably may work as might a standard circle circuit with the carbon dioxide filter by-passed or removed; however fresh gas will be wasted and the efficiency would be reduced.

When minute ventilation is greater than or equal to fresh gas flow, the above-mentioned preferred circuit prevents loss of fresh gas and ensures that the patient receives all the fresh gas independent of the pattern of breathing since fresh gas alone enters the fresh gas reservoir, and exhaled gas enters its own separate reservoir. The fresh gas reservoir bag is large enough to store fresh gas for 5–10 seconds or more of reduced ventilation or total apnea, ensuring that even under these circumstances fresh gas will not be lost. The preferred circuit prevents rebreathing at a minute ventilation equal to the fresh gas flow because the check valve in the interconnecting conduit does not open to allow rebreathing of previously exhaled gas unless a negative pressure exists on the inspiratory side of the conduit of the circuit. Also, when minute ventilation exceeds the fresh gas flow, a negative pressure occurs in the inspiratory conduit, opening the conduit's check valve. The circuit provides that after the check valve opens, alveolar gas is rebreathed in preference to dead space gas because the interconnecting conduit is located such that exhaled alveolar gas will be closest to it and dead space gas will be furthest from it. The exhaled gas reservoir is preferably sized at 3 L which is well in excess of the volume of an individual's breath, therefore it is unlikely that the patient shall be able to breathe any room air entering via the opening at the end of the exhaled gas reservoir.

The basic approach of preventing a decrease in $PCO_2$ with increased ventilation is similar as that taught by Fisher (WO98/41266). In brief, only breathing the fresh gas contributes to alveolar ventilation (VA) which establishes a gradient for $CO_2$ elimination. All gas breathed in excess of the fresh gas entering the circuit, or the fresh gas flow, is rebreathed gas. Fisher (WO98/41266) has in his prior application taught that the closer the partial pressure of $CO_2$ in the inhaled gas to that of mixed venous blood ($PvCO_2$), the less the effect on $CO_2$ elimination. Fisher (WO98/41266) expressed the relationship of alveolar ventilation, minute ventilation (V) and $PCO_2$ of rebreathed gas as follows:

$$VA = FGF + (V-FGF)(PvCO_2 - PCO_2 \text{ of exhaled gas})/PvCO_2$$

(Where FGF stands for the fresh gas flow, and other terms as described previously)

It is clear from this equation that as the $PCO_2$ of the exhaled gas approaches that of the mixed venous blood, the alveolar ventilation is determined only by the fresh gas flow and not the minute ventilation.

As one exhales, the first gas to exit the mouth comes from the trachea where little gas exchange has occurred. The $PCO_2$ of this gas is close to that of the inhaled gas and is termed "dead space gas". The last gas to exit the mouth has had the most time to equilibrate with mixed venous blood, has a $PCO_2$ closest to that of mixed venous blood and is termed "alveolar gas". Gas exhaled between these two periods has a $PCO_2$ intermediate between the two concentrations. The equation cited above explains why rebreathing alveolar gas would be the most effective in maintaining the $PCO_2$ at a constant level when minute ventilation increases.

Accordingly, in the circuit of the present invention:
1. All of the fresh gas is inhaled by the subject when minute ventilation is equal to or exceeds fresh gas flow;
2. The "alveolar gas" is preferentially rebreathed when minute ventilation exceeds the fresh gas flow;
3. When minute ventilation is equal to or greater than fresh gas flow, all the fresh gas contributes to alveolar ventilation.

DETAILED DESCRIPTION OF THE INVENTION

Figure 1:
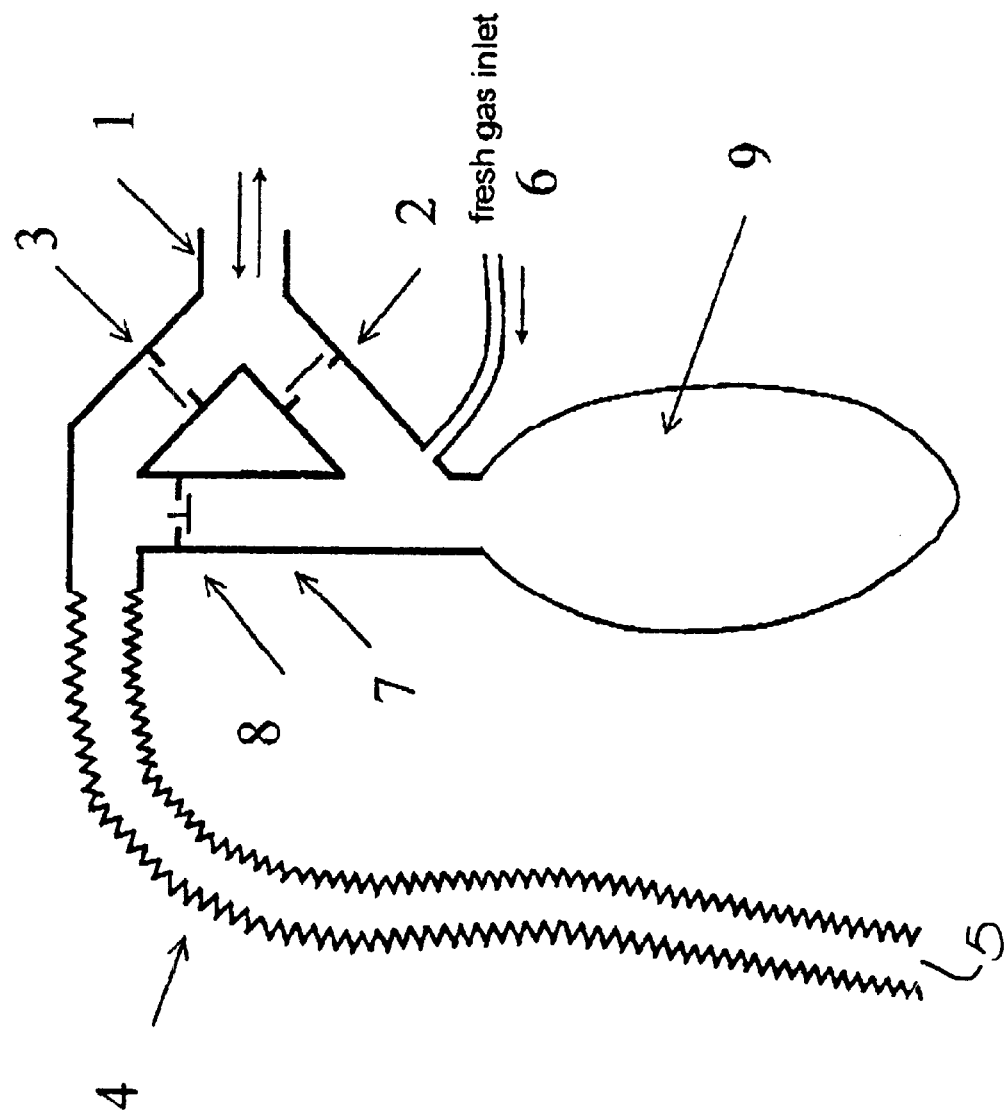
FIG. 1 illustrates schematically the nature of the breathing circuit and components of the present invention enabling the $PCO_2$ to remain constant despite increase in minute ventilation.

The patient breathes through one port of a Y-piece 1. The other two arms of the Y-piece contain one-way valves. The inspiratory limb of the Y-piece contains a one-way valve, the inspiratory valve 2 which directs gas to flow towards the patient when the patient makes an inspiratory effort but during exhalation acts as a check valve preventing flow in the opposite direction. The other limb of the Y-piece, the expiratory limb, contains a one-way valve, the expiratory valve 3, positioned such that it allows gas to exit the Y-piece when the patient exhales but acts as a check valve preventing flow towards the patient when the patient inhales. Immediately distal to the expiratory limb of the Y-piece is attached a large bore tubing 4, termed "reservoir" or "reservoir tube" that is open at its distal end 5. The reservoir tube may be fabricated from rigid or flexible tubing or as a collapsible bag and is preferably greater than 22 mm in diameter, and its length is such that the total volume of the tubing is about or greater than 3 L when it is being used for an average (70 Kg) adult. Larger volumes of reservoir tubing will be required for larger subjects and vice versa. The inspiratory port is connected to a source of fresh gas 6, i.e., gas not containing $CO_2$, flowing into the circuit at a fixed rate and a fresh gas reservoir bag 9 of about 3 L in volume. A bypass conduit 7 connects the expiratory limb and the inspiratory limb. The opening of the conduit to the expiratory limb is preferably as close as possible to the expiratory one-way valve. This conduit contains a one-way valve 8 allowing flow from the expiratory to the inspiratory limb. The conduit's one-way valve requires an opening pressure differential across the valve slightly greater than that of the inspiratory valve. In this way, during inspiration, fresh gas, consisting of fresh gas flow and the contents of the fresh gas reservoir bag, is preferentially drawn from the inspiratory manifold.

Circuit function.

When the subject's minute ventilation is equal to or less than the fresh gas flow (FGF), only fresh gas (FG) is breathed. During exhalation FG accumulates in the FG reservoir. During inhalation fresh gas flowing into the circuit and the contents of the fresh gas reservoir are inhaled. When minute ventilation exceeds FGF, on each breath, FG is breathed until the FG reservoir is emptied. Additional inspiratory efforts result in a decrease in gas pressure on the inspiratory side of the circuit. When this pressure differential across the bypass conduit's valve exceeds its opening pressure, the one-way valve opens and exhaled gas is drawn back from the expired gas reservoir into the inspiratory limb of the Y-piece and hence to the patient. The last gas to be exhaled during the previous breath, termed "alveolar gas" is the first to be drawn back into the inspiratory limb and inhaled (rebreathed) by the subject.

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

What is claimed is:

1. A method of controlling partial pressure of carbon dioxide in a patient at a predetermined desired level(s), comprising drawing back an alveolar gas exhaled by the patient into a fresh gas flow for the patient to inhale when a minute ventilation of the patient is no less than the fresh gas flow.

2. The method of claim 1, further comprising a step of preventing a gas exhaled by the patient from being supplied to the fresh gas flow when the minute ventilation is less than the fresh gas flow.

3. A breathing circuit, comprising:
   a port through which a patient exhales an inhalation gas and exhales an exhalation gas;
   an inspiratory limb having a first end connected to the port and a second end, the inspiratory limb supplying the inhalation gas to the patient;
   an expiratory limb having a first end connected to the port and a second end, the patient exhaling the exhalation gas to the expiratory limb;
   a bypass conduit connecting the inspiratory limb and the expiratory limb at the second ends thereof; and
   a one-way check valve disposed in the bypass conduit in a proximity of the second end of the expiratory limb, the one-way check valve being operative to direct the exhalation gas into the inspiratory limb when a pressure differential applied thereon reaches a predetermined level.

4. The breathing circuit of claim 3, wherein the inspiratory limb further comprises a one-way check valve operative to prevent the inhalation gas flowing from the first end to the second end of the inspiratory limb.

5. The breathing circuit of claim 3, wherein the expiratory limb further comprises a one-way check valve operative to prevent the exhalation gas flowing from the second end to the first end of the expiratory limb.

6. The breathing circuit of claim 3, further comprising:
   a fresh gas inlet connected to the inspiratory limb for supplying a fresh gas; and
   a reservoir bag connected to the second end of the inspiratory limb for storing the fresh gas.

7. The breathing circuit of claim 3, further comprising a reservoir tube with a first end connected to the second end of the expiratory limb for retaining a predetermined part of the exhalation gas and an open second end.

8. The breathing circuit of claim 7, wherein the reservoir tube is made of a rigid tubing material or a flexible tubing material.

9. The breathing circuit of claim 7, wherein the reservoir tube includes a collapsible bag with a diameter larger than 22 mm.

10. The breathing circuit of claim 7, wherein the reservoir tube has a total volume determined according to the weight of the patient.

11. The breathing circuit of claim 7, wherein the reservoir tube has a total volume of about 3 L.

12. A method of enhancing a diagnostic procedure or medical treatment comprising the steps of:
    providing a breathing circuit with an inspiratory path for supplying an inhalation gas to a patient and an expiratory path to which the patient exhaling an exhalation gas;
    supplying a fresh gas as the inhalation gas for the patient to breathe;
    drawing back a last exhalation gas exhaled by the patient in a previous breathing cycle as a part of the inhalation gas for the patient to rebreathe; and
    increasing the flow of the last exhalation gas to be rebreathed by reducing the flow of the fresh gas when the patient is ventilating at a rate greater than the flow of the fresh gas and inducing hypercapnia to the patient is required.

13. A method of treating a patient during a traumatic event characterized by hyperventilation comprising the steps of:
    providing a fresh gas to the patient, the flow of the fresh gas being equal to an alveolar ventilation of the patient;
    introducing an alveolar gas exhaled by the patient into the fresh gas to prevent the alveolar ventilation from increasing due to increase of a minute ventilation of the patient; and
    continuously introducing the alveolar gas into the fresh gas until the traumatic event is terminated.

14. The method of claim 13, wherein the traumatic event includes shivering and tremors during labor, post-anesthesia, and hypothermia.

15. The method of claim 13, wherein the traumatic event includes fetal distress due to asphyxia.

16. The method of claim 13, wherein the step of introducing an alveolar gas further comprises: inducing cerebral vasodilatation, preventing cerebral vasospasm, and providing cerebral protection following subarachnoid hemorrhage, and cerebral trauma.

17. The method of claim 13, wherein the step of introducing an alveolar gas further comprises increasing tissue perfusion in tissues containing cancerous cells to increase sensitivity thereof for ionizing radiation and delivery of chemotherapeutic agents.

18. The method of claim 13, wherein the step of introducing an alveolar gas further comprises providing contrast between tissues with normal and abnormal vascular response to aid radiodiagnostic procedures.

19. A method of controlling partial pressure of carbon dioxide of a patient at a predetermined desired level, comprising the steps of:
    supplying only a fresh gas from a gas input to the patient during an inspiratory phase thereof when a minute ventilation is equal to or less than a flow rate of the fresh gas supplied by the gas input;
    accumulating the fresh gas in a fresh gas reservoir during an expiratory phase of the patient;
    collecting an alveolar gas exhaled from the patient at an end of the expiratory phase;
    providing only the fresh has supplied from the gas input to the patient during a next inspiratory phase when the minute ventilation is equal to or less than the flow rate of the fresh has supplied by the gas input;
    supplying the fresh gas accumulated in the fresh gas reservoir when the minute ventilation exceeds the flow rate of the fresh gas supplied from the gas input; and
    adding the alveolar gas for the patient to rebreathe.

20. The method of claim 19, wherein the step of adding the alveolar gas is performed when the fresh gas reservoir is emptied during the next inspiratory phase.

* * * * *